United States Patent [19]

Pettersen et al.

[11] Patent Number: 5,324,859

[45] Date of Patent: Jun. 28, 1994

[54] DEUTERATED BENZALDEHYDES

[75] Inventors: Erik O. Pettersen, N-Oslo; Rolf O. Larsen, Langesund; John M. Dornish, Bekkestua; Bernt Borretzen, Heistad; Reidar Oftebro, Hvalstad; Thomas Ramdahl, Eiksmarka, all of Norway

[73] Assignee: Norsk Hydro A.S., Oslo, Norway

[21] Appl. No.: 5,978

[22] Filed: Jan. 19, 1993

[30] Foreign Application Priority Data

Jan. 21, 1992 [GB] United Kingdom ............... 9201275

[51] Int. Cl.$^5$ ................ C07C 47/54; C07C 47/542
[52] U.S. Cl. .................... 568/425; 564/305; 564/374; 564/502; 568/442
[58] Field of Search ............ 568/425, 426, 424, 435, 568/437, 425, 826, 442; 564/305, 502, 374

[56] References Cited

U.S. PATENT DOCUMENTS 5,138,099  8/1992  Lang .................. 568/425
5,191,126  3/1993  Papenfuhs et al. ......... 568/425

FOREIGN PATENT DOCUMENTS 0145334  6/1985  European Pat. Off. .......... 568/425

Primary Examiner—Werren B. Lone
Attorney, Agent, or Firm—Wenderoth, Lind & Ponack

[57] ABSTRACT

New compounds of formula I:

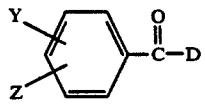

(I)

wherein
Y may be CN or

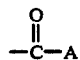

wherein A may be H, D, alkyl with 1–4 carbon atoms, OR wherein R is H or alkyl with 1–4 carbon atoms, or —NR$_1$R$_2$ or —CR$_1$R$_2$R$_3$ wherein R$_1$, R$_2$ and R$_3$ are the same or different and are H or alkyl with 1–4 carbon atoms;

Z is H, D, Y or alkyl with 1–4 C-atoms, halogen, nitro, amino, monoalkyl amino or dialkyl amino wherein the alkyl groups have 1–4 C atoms, or —OR wherein R may be H or alkyl with 1–4 C-atoms or —CR$_4$, R$_5$R$_6$ wherein R$_4$, R$_5$ and R$_6$ may be the same or different and may be H or F;

and pharmaceutically acceptable salts thereof, are useful as anti-cancer agents or as intermediates for preparing anti-cancer agents.

2 Claims, No Drawings

DEUTERATED BENZALDEHYDES

The present invention concerns new compounds which may be used as anti-cancer agents or intermediates in the preparation of compounds useful as anti-cancer agents or as agents useful in the treatment of illnesses which arise due to an elevated cell proliferation. The compounds according to the present invention are deuterated benzaldehydes, which carry a carboxyl group, derivative or analogue on the phenyl group.

TECHNICAL FIELD

It is known from EP215395, J63264411, J88009490, J55069510 and EP283139, among others, that benzaldehydes and derivatives thereof have an anti-cancer effect. These compounds exert a growth-inhibitory effect on human cells which is by its nature reversible. Growth inhibition induced by these compounds is primarily due to a reduction in the protein synthesis by cells. (Pettersen et al., Eur. J.Clin. Oncolo. 19, 935–940 (1983) and Cancer Res. 45, 2085–2091 (1985)). The inhibition of protein synthesis is only effective as long as these agents are present in the cellular microenvironment. The synthesis of cellular protein is, for instance, rapidly restored to its normal level within one hour from the time when the agent is removed from the cells.

This leads to the effect that the normal cells are left without damage after treatment with such compounds. Furthermore, the inhibition of protein synthesis achieved induces a prolonged cell cycle duration such that a reduction of the cell production as well as a reduction of protein synthesis is achieved during treatment. Therefore according to UK Patent application 9026080.3, also diseases for which the symptomatic cause is an enhanced cell proliferation rate can be treated with derivatives of benzaldhydes without this leading to cell death—a condition unwanted since the cells involved are normal cells with an abnormal cell proliferation rate. Examples of such diseases are psoriasis, inflammatory diseases, rheumatic diseases and allergic dermatologic reactions.

In EP283139 it was reported that the substitution of the aldehyde hydrogen with a deuterium lead to an even stronger inhibition of the protein synthesis. Further, it was reported that the new acetals had a longer half life in the cells.

It has now surprisingly been found that the introduction of a carboxylic group, derivative or analogue as a substituent on the phenyl group in such compounds gives a stronger inhibition of the protein synthesis.

DETAILED DESCRIPTION

The compounds of the present invention have the general formula (I):

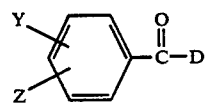

(I)

wherein
Y may be —CN or

wherein A may be H, D, alkyl with 1–4 carbon atoms, —OR wherein R is H or alkyl with 1–4 carbon atoms, or —NR$_1$R$_2$ or —CR$_1$R$_2$R$_3$ wherein R$_1$, R$_2$ and R$_3$ are the same or different and are H or alkyl with 1–4 carbon atoms;

Z is H, D, Y or alkyl with 1–4 C-atoms, halogen, nitro, amino, monoalkyl amino or dialkyl amino wherein the alkyl groups have 1–4 C-atoms, or OR wherein R may be H or alkyl with 1–4 C-atoms, or CR$_4$R$_5$R$_6$ wherein R$_4$, R$_5$ and R$_6$ may be the same or different and may be H or F;

and pharmaceutically acceptable salts thereof.

The phenyl ring of the compounds of formula I may carry one or several groups Z, at most four Z groups. It is most preferred when there are several Z groups present that these groups are the same or that at least one of them is a further carboxylic group or derivative or analogue.

As shown by formula I above the carboxylic group, derivative or analogue substituent(s) Y includes groups such as carboxylic acids, ester, keto groups, acid halogenids, amides, aldehydes and cyano groups.. In the remainder of the text, these groups will for convenience simply be denoted "carboxylic groups".

When Z is deuterium this means that the phenyl ring may be partly or fully deuterated, carrying at the most four deuterium atoms on the phenyl ring.

When any group is alkyl it is most preferred as being methyl or ethyl.

The halogen may be any of chlorine, bromine, iodine or fluorine.

The carboxylic group, Y, may be in the positions 2, 3 or 4 for compounds of formula I wherein Z is H, but the most preferred position is number 4.

In compounds of formula I, wherein Z is not H, the carboxylic group, Y, may be in any of the 2, 3, 4, 5 or 6 positions.

When there is more than one substituent Z, two of which are carboxylic groups, most preferred positions for these two groups will be in the 2 and 6 positions or the 3 and 5 positions depending on the position and influence of the other substituent Z and the Y group.

The compounds of formula I may be prepared by procedures well-known to those skilled in the art, such as:

(1) the Rosenmund reduction of the corresponding acid chloride, see [E. Mosettig and R. Mozingo in Organic Reactions, Vol. 4, Ch. 7, John Wiley & Son];

(2) H/D exchange of the corresponding non-deuterated aldehyde via diathiane derivatives by utilizing the increased acidity of the aldehydric proton in the diathiane ring.

[D. Seebach, B. W. Erickson and G. Singh, J. Org. Chem., Vol. 31, p. 4303, (1966)]; and (3) electrophilic substitutions in substituted aromatic ring leading to the introduction of deuterated formyl group. (Gatterman reactions)

The compounds according to this invention may be used as anti-cancer agents, and thus the invention also comprises the use of a compound of formula I for the manufacture of an anti-cancer agent, and pharmaceutical compositions comprising a compound of formula I alone or in admixture with a pharmaceutically acceptable carrier, diluent and/or excipient.

The compounds according to the present invention may also be used as intermediates for the preparation of the corresponding benzaldehyde derivatives, and thus in one aspect the invention is the use of a compound of formula (I) as an intermediate in the preparation of a substituted benzaldehyde acetal according to formula (II):

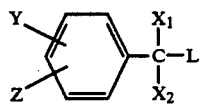

wherein
L may be H or D;
Y may be CN or

wherein A may be H, D, alkyl with 1-4 carbon atoms, OR wherein R is H or alkyl with 1-4 carbon atoms, or $NR_1R_2$ or $CR_1R_2R_3$ wherein $R_1$, $R_2$ and $R_3$ are the same or different and are H or alkyl with 1-4 carbon atoms;

Z is H, D, Y or alkyl with 1-4 C-atoms, halogen, nitro, amino, monoalkyl amino or dialkyl amino wherein the alkyl groups have 1-4 C atoms, or OR wherein R may be H or alkyl with 1-4 C-atoms, or $-CR_4R_5R_6$ wherein $R_4$, $R_5$ and $R_6$ may be the same or different and may be H or F;

$X_1$ and $X_2$ may be the same or different and may be $-OR$, $-NR_1R_2$ or $-SR$ wherein R, $R_1$ and $R_2$ may be the same or different and may be alkyl with 1-22 C atoms; or $X_1$ and $X_2$ may together with the carbon atom to which they are bound form a cyclic acetal (O,O), thioacetal (S,O), dithiane (S,S), aminal (N,N), oxazolidine (O,N) or thiazolidine (N,S);

and pharmaceutically acceptable salts thereof.

Processes for preparing cyclic or acyclic oxygen acetals from aldehydes include reacting the substituted benzaldehyde or a lower acetals of the benzaldehyde with an alcohol in the presence of an acidic catalyst. In the case of cyclic derivatives said alcohol must be a di-or polyhydric alcohol. These reactions may conveniently be carried out in a dipolar solvent such as dimethyl formamide, dimethyl sulphoxide, dimethyl acetamide or the like.

Similarly, the preparation of the oxazolidines, animals, oxathiolanes, dithianes and thiazolidines proceeds in a conventional manner by reacting the substituted benzaldehyde, which may be further substituted, with the corresponding aminoalcohols, diamines, thioalcohols, dithiols and thioamines respectively. In the case of the acyclic heteroacetals, these may be prepared by reacting the corresponding aldehyde according to this invention with a thioalcohol or secondary amine.

These reactions may be carried out in solvents which form an azeotropic mixture with the water formed in the reaction. Typical solvents used are inert hydrocarbons, preferably benzene or toluene, which are capable by azeotropically removing the water formed, to drive the reaction to a completion.

The reaction conditions and solvents used will in each individual reaction depend on the reactivity and solubility of the reactants.

Generally the compounds according to the present invention may used as intermediates as shown below in the reaction scheme for the preparation of substituted benzylidene ascorbic acid acetals:

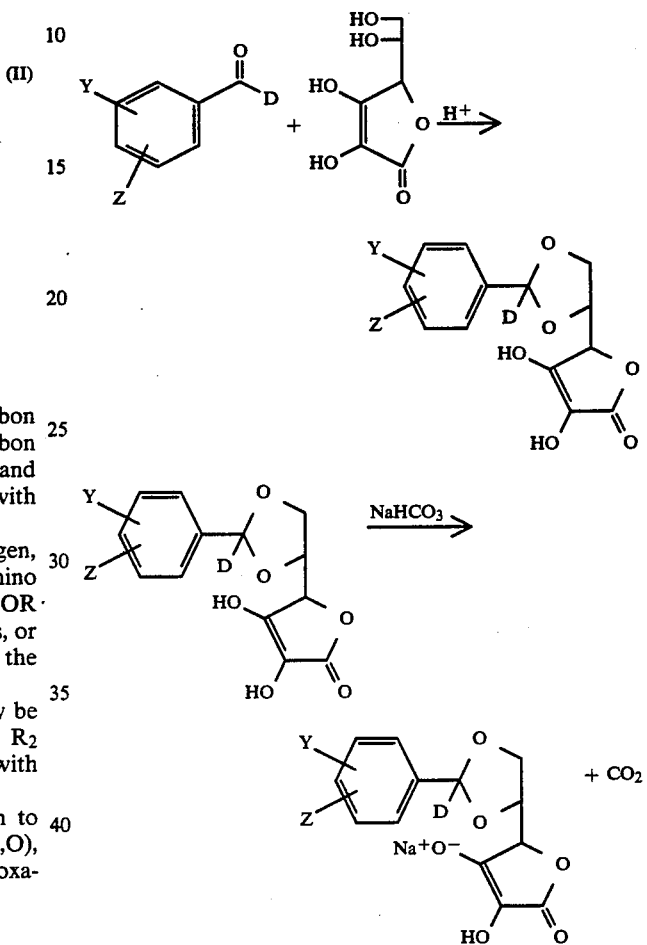

The following examples are illustrative for how the compounds of the present invention may be prepared.

EXAMPLE 1

Preparation of Isophthalaldehyde-$d_2$

STEP 1: PREPARATION OF ISOPHTHALDEHYDE-(BIS-1,3-PROPANE-DITHIOACETAL)

Isophthaldehyde (10 g, 0.075 mole), 1,3-propanedithiol (15 ml, 0.15 mole), paratoluen sulphonic acid (spatual tip) and toluene (150 ml) were mixed and boiled under reflux for 20 hours. A small amount of hexane and a few drops of diisopropyl ester were added, and the solution cooled. The crystals which precipitated were filtered and dried.

The preparation gave 17 g of the title compound, 74% of theoretical yield.

STEP 2: PREPARATION OF ISOPHTHALDEHYDE-(BIS-1,3-PROPANE-DITHIOACETAL)$d_2$

Isophthaldehyde-(bis-1,3-propanedithioacetal) (10 g, 32 mmole) was dissolved in dry tetrahydrofuran (THF) (200 ml) in a 500 ml three-necked round-bottomed flask equipped with septum. The apparatus was dry and under argon. The solution was cooled to −60° C. Butyl lithium (60 ml 1.6M BuLI, 96 mmole) was added slowly via the septum, while the temperature was held at −50° C. After three hours a precipitate had formed (the lithium salt of dithiane). After a reaction time of 4 hours the temperature had reached −30°. $D_2O$ (30 ml) was added and stirred until the temperature had reached +5° C. The reaction mixture was filtered, leaving wet crystals. The raw product was dissolved in dichloromethane, washed with 2M hydrochloric acid and water, dried with magnesium sulphate and evaporated to dryness leaving 6 g of product. This was recrystallised from ethylacetate giving 4 g of brilliant white crystals.

The mother liquor was worked-up by evaporation and recrystallisation giving 2.9 g product.

The preparation gave a total yield of 6.9 g, 68% of theoretical.

STEP 3: SYNTHESIS OF DEUTERATED ISOPTALALDEHYE (Ref. A.V.Rama Rao et al., Tetrahedron, 43,779(1987))

Isophtaladehyde-bis-dithioacetal-$d_2$, (1.8 g, 0.057 moles), $HgCl_2$, (6.8 g, 0.025 moles), and HgO (2.7 g, 0.013 moles) were dissolved in a 9:1 mixture of acetonitril and water. The reaction mixture was boiled at reflux for 1.5 h. After the reaction mixture has been cooled to room temperature, the insoluble mercury salts are filtered off. The filtrate is then washed twice with a 5% ammonium acetate solution. After removing the formed crystals, the product is taken up in dichloromethane. The organic phase is then evaporated to dryness, giving yellow crystals. The product is finally recrystallised from dichloromethane, giving 0,5 g of slightly yellow crystals, mp. 86°–87° C.

The GC-MS of the product shows one peak with the molecular ion in the mass spectrum at m/e 136, which confirms the structure of iso-phtaladehyde-$d_2$, $C_8H_4D_2O_2$, Mw. 136.

EXAMPLE 2

Preparation of Methyl-4-formylbenzoate-$d_1$

STEP 1: PREPARATION OF 4-CARBOMETHOXYBENZOYLCHLORIDE

Monomethyl terephthalate (10.2 g, 0.057 mol) and thionylchloride (50 ml) were mixed in a 100 ml three-necked flask and stirred under gentle reflux overnight. The cooling water was shut off and excess thionylchloride swept away in a stream of nitrogen. By raising the temperature, the product then was distilled and collected as white crystals of high purity.

Yield: 7.2 g, 64% of theoretical

STEP 2: PREPARATION OF METHYL-4-FORMYLBENZOATE-$d_1$

4-Carbomethoxy benzoylchloride (7.2 g, 0.036 mol), quinolinesulphur * (37 µl stock solution), 5% Pd on $BaSo_4$ (370 mg) and a mixture of deuterated aromatic solvents (100 ml) were refluxed under mechanical stirring in a 250 ml three-necked flask. Deuterium gas was bubbled through, and the reaction followed by GC. Simultaneously, the exhaust gas was bubbled into water (100 ml) in a separate flask and analysed by titrating with 1N NaOH.

*A stock solution was made by refluxing sulphur (1 g) in freshly distilled quinoline (6 g) for 5 hours and diluting to 70 ml in a mixture of deuterated aromatic solvents.

After 29 hours, the reaction was nearly completed. The catalyst was then filtered off and the filtrate vigorously stirred for 3 days with a $Na_2S_2O_5$-solution in heavy water (20 g). The aldehyde-sulphite complex thus formed was isolated by filtering and decomposed by stirring for 4 hours with 5% $Na_2CO_3$ solution in heavy water (100 ml). The milky suspension was extracted with ether (3×300 ml) and the combined extracts dried ($MgSo_4$), filtered and evaporated to give the pure aldehyde as a white solid, mp. 62°–63.5° C. Yield: 3.95 g, 66% of theoretical. The degree of deuteration was 96.3%, as analysed by NMR.

The following Examples show the use of the compounds of formula I as intermediates in the preparation of compounds of formula II.

EXAMPLE 3

Reaction of Isophthalaldehyde-$d_1$ to form 5,6-sodium-(3-deuteroformyl)-benzylidene-L-ascorbate-$d_1$.

PREPARATION OF SODIUM 5,6-(3-DEUTEROFORMYL)-BENZYLIDENE-L-ASCORBATE-$d_1$

To a solution of isophthalaldehyde-$d_2$ (6.0 g, 0.044 mol) and L-ascorbic acid (7.7 g, 0.044 mol) in N,N-dimethylformamide (65 ml) was carefully added conc. $D_2SO_4$ (1 ml) and the mixture stirred at room temperature under $N_2$ for 2 days. The reaction mixture was evaporated in the vacuum from a water jet for 2 days, then from an oil pump overnight, giving a viscous residue. The pH was raised to about 6 by the careful addition of 10% $NaHCO_3$ and the solution evaporated overnight. The residue was dissolved in 7.5% methanol/water (50 ml), filtered on a 0.45 µm Millipore filter and evaporated to give a 76% pure yellow solid (12.2 g). This crude product was purified by preparative chromatography on a prepacked reversed phase column (Lobar C) eluting with 7.5% methanol/water.

By freeze-drying and combining the product fractions, a total of 2.1 g pure substance was collected (15% of theoretical). The degree of deuteration was indicated by NMR to be better than 96%.

EXAMPLE 4

Reaction of Methyl-formyl-benzoate-$d_1$ to form sodium-5,6-(4-carbomethoxy)-benzylidene-L-ascorbatye-$d_1$.

PREPARATION OF SODIUM-5,6-(4-CARBOMETHOXY)-BENZYLIDENE-L-ASCORBATE-$d_1$

Methyl-4-formylbenzoate-$d_1$ (6.0 g, 0.036 mol) and L-ascorbic acid (6.4 g, 0.036 mol) were dissolved in dry dimethylformamide (50 ml) in a 250 ml flask. Conc. sulphuric acid (0.5 ml) was carefully added, and the reaction mixture left on the rotary evaporator connected to a water jet vacuum source for 3 days. The solvent was then driven off by evaporating overnight using an oil pump. To the viscous water (75 ml) was added dropwise, raising the pH to 6. The solution was freeze-dried and the crude product rinsed on a prepacked reversed phase column (Lobar C), eluting with 5% methanol/water. Product fractions from 6 runs were freeze-dried and combined to give the title compound as a fluffy solid, 6.2 g, 50% of the theoretical yield. The degree of deuteration was shown by NMR to be 98.1%.

Biological experiments

In the following in vitro experiments, the rate of protein synthesis was measured for a compound from the prior art, which is deuterated benzaldehyde and for deuterated isophthalaldehyde, a compound according to the invention.

Cell Culturing Techniques and Synchronization

Human cells of the established line NHIK 3025, originating from a cervical carcinoma in situ (Nordbye, K. and Oftebro, R., Exp. Cell Res., 58: 458, 1969), Oftebro, R. and Nordbye, K., Exp. Cell Res., 58: 459-460, 1969) were cultivated in medium E2a (Puck et al., J. Exp. Med., 106: 145-165, 1957) supplemented with 20% human (prepared at the laboratory) and 10% horse serum (Grand Island Biological Co.).

The cells are routinely grown as monolayers in tissue culture flasks. The cells were kept in continuous exponential growth by frequent reculturing, i.e. every second and third day, and were obtained by repeated selection of mitotic cells (Pettersen et al., Cell Tissue Kinet., 10: 511-522, 1977). During reculturing as well as during experiments the cells were kept in a walk-in incubator at 37° C. Under growth conditions as used here, the NHIK 3025 cells have a medium cell-cycle time of ~18 hr, with medium $G_1$, $S_1$ and $G_2$ durations of ~7, ~8 and ~2.5 hr, respectively.

Protein Synthesis

The rate of protein synthesis was calculated as described previously (R nning et al., J. Cell Physiol., 107: 47-57, 1981). Briefly, cellular protein was labeled to saturation during a 2-day preincubation with [$^{14}$C]valine of constant specific radioactivity (0.5 Ci/mol) prior to the experiment. This was achieved by using a high concentration of valine so that the dilution of [$^{14}$C]valine by intracellular valine and by proteolytically generated valine will be negligible (R nning etal., Exp. Cell Res., 123: 63-72, 1979), thus keeping the specific radioactivity at a constant level. The rate of protein synthesis was calculated from the incorporation of [$^3$H]valine of constant specific activity. The incorporated measurements were related to the total of [$^{14}$C] radioactivity in protein at the beginning of the respective measurement periods and expressed as the percentage per hr (R nning et al., J. Cell. Physiol., 107: 47-57, 1981).

Results

The protein synthesis inhibition induced by benzaldehyde-$d_1$ and isophthalaldehyde-$d_2$ was measured in human NHIK 3025 cells after administration of the compounds. In table 1 the rate of protein synthesis is given in per cent relative to an untreated control. The values presented represent one experiment, and are a mean of 3 samples ± standard error. Even though the compound according to the invention is administered at a much lower concentration, the protein synthesis inhibition is much stronger and correspondingly the anti-cancer effect.

TABLE 1

| SUBSTANCE | FORMULA | CONC. [Mm] | RATE OF PROTEIN SYNTHESIS [%] |
|---|---|---|---|
| ISOPHTHAL-$d_2$ | (benzene ring with C=D and ODC groups) | 1.0 | 26.6 ± 1.0 |
| BENZALDEHYDE-$D_1$ | (benzene ring with C=O, C-D group) | 2.5 | 52.5 ± 4.3 |

Several other experiments have shown the same general effect.

According to present invention the compounds of formula I may be administered to a patient in need of anti-cancer treatment or to a patient suffering from diseases which arise due to an abnormally elevated cell proliferation.

For this purpose the compounds may be formulated in any suitable manner for administration to a patient either alone or in admixture with suitable pharmaceutical carriers or adjuvants.

It is especially preferred to prepare the formulations for systemic therapy either as oral preparations or parenteral formulations.

Suitable enteral preparations will be tablets, capsules, e.g. soft or hard gelatine capsules, granules, grains or powders, syrups, suspensions, solutions or suppositories. Such will be prepared as known in the art by mixing one or more of the compounds of formula I with non-toxic, inert, solid or liquid carriers.

Suitable parental preparations of the compounds of formula I are injection or infusion solution.

When administered topically the compounds of formula I may be formulated as a lotion, salve, ointment, cream, gel, tincture, spray or the like containing the compounds of formula I in admixture with non-toxic, inert, solid or liquid carriers which are usual in topical preparations. It is especially suitable to use a formulation which protects the active ingredient against air, water and the like.

The preparations can contain inert or pharmacodynamically active additives. Tablets or granulates e.g. can contain a series of binding agents, filler materials, carrier substances and/or diluents. Liquid preparations may be present, for example, in the form of a sterile solution. Capsules can contain a filler material or thickening agent in addition to the active ingredient. Furthermore, flavour-improving additives as well as the substances usually used as preserving, stabilizing, moisture-retaining and emulsifying agents, salts for varying the osmotic pressure, buffers and other additives may also be present.

The dosages in which the preparations are administered can vary according to the indication, the mode of use and the route of administration, as well as to the requirements of the patient. In general a daily dosage for a systemic therapy for an adult average patient in need of anti-cancer treatment will be about 0.1-500 mg/kg body weight/day, preferably 2-200 mg/kg body weight/day.

The daily dosage for a systemic therapy for an adult average patient in need of treatment for elevated cell-proliferation will be about 0.1-50 mg/kg/day preferably 1-15 mg/kg/day. For topic administration, the suitable salve can contain from 0.1-50% by weight of the pharmaceutical formulation, especially 1-20%.

If desired the pharmaceutical preparation of the compound of formula I can contain an antioxidant, e.g. tocopherol, N-methyl-tocopheramine, butylated hydroxyanisole, ascorbic acid or butylated hydroxytoluene.

We claim:

1. A compound of the formula

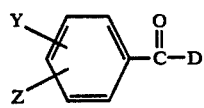

wherein

Y is a member selected from the group consisting of (1) CN, (2)

wherein A is H, D, alkyl of 1–4 carbon atoms or OR wherein R is H or alkyl of 1–4 carbon atoms, (3) $-NR_1R_2$ and (4) $-CR_1R_2R_3$ wherein $R_1$, $R_2$ and $R_3$ are the same or different and are H or alkyl of 1–4 carbon atoms; and Z is a member selected from the group consisting of (1) H, (2) D, (3) Y as defined above, (4) halogen, (5) nitro, (6) amino, (7) monoalkyl amino wherein the alkyl is of 1–4 carbon atoms, (8) dialkyl amino wherein the alkyl groups are of 1–4 carbon atoms, (9) —OR wherein R is H or alkyl of 1–4 carbon atoms and (10) $-CR_4R_5R_6$ wherein $R_4$, $R_5$ and $R_6$ are the same or different and are H or F, or a pharmaceutically acceptable salt thereof.

2. A pharmaceutical composition which comprises a pharmaceutically effective amount of a compound or salt thereof as defined in claim 1 and at least one member selected from the group consisting of a pharmaceutically acceptable carrier, diluent and excipient.

* * * * *

UNITED STATES PATENT AND TRADEMARK OFFICE
CERTIFICATE OF CORRECTION

PATENT NO. : 5,324,859
DATED : June 28, 1994
INVENTOR(S) : ERIK OLAI PETTERSEN, ROLF OLAF LARSEN, JOHN MICHAEL DORNISH, BERNT BORRETZEN, REIDAR OFTEBRO and THOMAS RAMDAHL It is certified that error appears in the above-indentified patent and that said Letters Patent is hereby corrected as shown below:

Column 7, lines 21 and 22, change "medium" to —median—;

lines 26, 34 and 43, change "R nning" to —Rønning—;

line 34, change "etal." to —et al.—;

Columns 7 and 8, in TABLE 1, under the heading "CONC.", change "Mm" to —mM—.

Signed and Sealed this

Seventh Day of February, 1995

Attest:

BRUCE LEHMAN

Attesting Officer     Commissioner of Patents and Trademarks